United States Patent
Bombardelli et al.

(10) Patent No.: US 9,901,610 B2
(45) Date of Patent: Feb. 27, 2018

(54) FORMULATIONS FOR THE TREATMENT AND PREVENTION OF OBESITY

(71) Applicant: INDENA S.P.A., Milan (IT)

(72) Inventors: Ezio Bombardelli, Gropello Cairoli (IT); Fabrizio Corti, Milan (IT)

(73) Assignee: INDENA S.P.A., Milan (IT)

( * ) Notice: Subject to any disclaimer, the term of this patent is extended or adjusted under 35 U.S.C. 154(b) by 0 days.

(21) Appl. No.: 14/433,179

(22) PCT Filed: Oct. 10, 2013

(86) PCT No.: PCT/EP2013/071138
§ 371 (c)(1),
(2) Date: Apr. 2, 2015

(87) PCT Pub. No.: WO2014/057024
PCT Pub. Date: Apr. 17, 2014

(65) Prior Publication Data
US 2015/0258157 A1 Sep. 17, 2015

(30) Foreign Application Priority Data

Oct. 12, 2012 (IT) .............................. MI2012A1727

(51) Int. Cl.
| | | |
|---|---|---|
| *A61K 36/254* | (2006.01) | |
| *A61K 36/258* | (2006.01) | |
| *A61K 36/87* | (2006.01) | |
| *A61K 36/28* | (2006.01) | |
| *A61K 36/00* | (2006.01) | |
| *A61K 36/48* | (2006.01) | |
| *A61K 36/85* | (2006.01) | |
| *A61K 9/20* | (2006.01) | |

(52) U.S. Cl.
CPC ............ *A61K 36/87* (2013.01); *A61K 9/2054* (2013.01); *A61K 36/258* (2013.01); *A61K 36/28* (2013.01); *A61K 36/48* (2013.01); *A61K 36/85* (2013.01); *A61K 2236/00* (2013.01)

(58) Field of Classification Search
None
See application file for complete search history.

(56) References Cited

U.S. PATENT DOCUMENTS

| | | | | |
|---|---|---|---|---|
| 4,157,894 A * | 6/1979 | Bombardelli | ........ | A61K 36/258 424/728 |
| 2009/0169657 A1* | 7/2009 | Berlanda | ................ | A23L 33/105 424/757 |
| 2009/0285911 A1* | 11/2009 | Bombardelli | ........ | A61K 36/185 424/725 |

FOREIGN PATENT DOCUMENTS

| | | | | |
|---|---|---|---|---|
| EP | 1967198 | 9/2008 | | |
| WO | WO 9920289 A1 * | 4/1999 | ........... | A61K 9/4858 |

OTHER PUBLICATIONS

Christensen et al. (2009) Phytother. Res. 23, 1316-1325.*
Barnes et al. (2005) J. Pharmacy and Pharmacol. 57: 929-954.*
Calleno et al. (2007) Int. J. Med. Sci. 4(1): 45-52.*
Heredia et al. (2012) Proc. Nutr. Soc. 71, 332-338.*
Marti et al. (2001) Obesity Reviews, 2, 131-140.*
Morazzoni et al. (2005) Fitoterapia 76: 401-411.*
Nieman et al. (1999) J. Amer. Diatetic Assoc. vol. 99, No. 3, 294-299.*
Sendogdu et al. (2006) Turkish J. Pharm. Sci. 3 (1): 7-18.*
Rondanelli, et al., Appetite Control and Glycaemia Reduction in Overweight Subjects trated with a Combination of Tow Highly Standardized Extracts from Phaseolus vulgaris and Cynara scolymus:, Phytotherapy Research, Feb. 1, 2011, pp. 1275-1282.
Carai, et al., "Multiple cycles of repeated treatments with a Phaseolus vulgaris dry extract reduce food intake and body weight in obese rats", British Journal of Nutrition, vol. 106, No. 05, May 3, 2011 pp. 762-768.
Fantini, et al., "Reducing Effect of a Phaseolus vulgaris Dry Extract on Food Intake, Body Weight, and Glycemia in Rats", Journal of Agricultural and Food Chemistry, vol. 57, No. 19, Oct. 14, 2009, pp. 9316-9323.
Moreno et al., "Inhibitory Effects of Grape Seed Extract on Lipases", Nutrition Elsevier Inc., US, vol. 19, Jan. 1, 2003, pp. 876-879.
Morazzoni, et al., "In vitro and in vivo immune stimulating effects of a new standardized Echinacea angustifolia root extract (Polinacea(TM)", Fitoterapia, IDB Holding, Milan, IT, vol. 76, No. 5, Jul. 1, 2005, pp. 401-411.
Kaushik et al., "Commonly consumed Indian plant food materials in the management of diabetes mellitus", Diabetes & Metabolic Syndrome: Clinical Research & Reviews, Elsevier, Amsterdam, NL, vol. 4, No. 1, Jan. 1, 2010, pp. 21-40.
Babish et al., "Antidiabetic Screening of Commercial Botanical Products in 3T3-L1 Adipocytes and db/db Mice", Journal of Medicinal Food, vol. 13, No. 3, Jun. 1, 2010, pp. 535-547.
Chrubasik S., "Clinical efficacy of a Phaseolus vulgaris and Cynara scolymus mixture on satiety", Focus on Alternative and Complementary Therapies 2012 Wiley-Blackwell USA, vol. 17, No. 1, Mar. 2012, pp. 75-77.
Anonymous: Polinacea, Indena, Jul. 24, 2012.
International Search Report and Written Opinion of PCT/EP2013/071138, dated Dec. 2, 2013.
Author Kaiyadeva, Title of publication—Kaiyadevanighantau, Page(s) being submitted—06 (p. No. 04-09), ( Ref.p. No. of publication:389 ), Publication Date—1979, Publisher—Chaukhambha Orientalia, Place of Publication—Varanasi, India.†
Author Vagbhata, Title of publication—Astanga Samgraha—(commentary by Indu) part-I(KA) [Time of origin 5-10th century ], Page(s) being submitted—07 (p. No. 10-16), ( Ref.p. No. of publication:68 ), Publication Date—1991, Publisher—Central Council for Research in Ayurveda & Siddha, Place of Publication—New Delhi, India.†
Author Vagbhata, Title of publication—Astanga Samgraha—(commentary by Indu) part-I(KA) [Time of origin 5-10th century ], Page(s) being submitted—06 (p. No. 17-22), ( Ref.p. No. of publication:68 ), Publication Date—1991, Publisher—Central Council for Research in Ayurveda & Siddha, Place of Publication—New Delhi, India.†

\* cited by examiner
† cited by third party

*Primary Examiner* — Chris R Tate
*Assistant Examiner* — Russell Fiebig
(74) *Attorney, Agent, or Firm* — Silvia Salvadori, P.C.; Silvia Salvadori

(57) ABSTRACT

Disclosed are compositions containing: a) *Phaseolus vulgaris* extract; b) *Cynara scolymus* extract; c) *Echinacea angustifolia* extract; d) *Vitis vinifera* extract and optionally e) *Panax ginseng* extract, mixed with suitable excipients.

7 Claims, No Drawings

FORMULATIONS FOR THE TREATMENT AND PREVENTION OF OBESITY

This application is a U.S. national stage of PCT/EP2013/071138 filed on 10 Oct. 2013, which claims priority to and the benefit of Italian Application No. MI2012A001727 filed on 12 Oct. 2012, the contents of which are incorporated herein by reference in their entireties.

The present invention relates to combinations of medicinal plant extracts useful in the prevention and treatment of obesity and excess weight.

PRIOR ART

Excess weight and obesity are rising to a worrying extent in all the industrialised countries, and may affect up to 50% of the population in the next decade. Obesity affects the health of the sufferer, with adverse effects on the cardiovascular, musculoskeletal and gastrointestinal systems.

Obesity is associated with a disorder of the lipid metabolism which, in turn, is influenced by a biochemical and hormonal profile involving glucose, insulin resistance, dyslipidaemia and neurovegetative mediators.

The onset of a state of excess weight/obesity at a young age is a highly significant risk factor for the activation of processes which, at adult age, can promote metabolic syndrome, type 2 diabetes and the development of adult obesity. Many metabolic, cardiovascular and oncological disorders seem to be closely related to insulin resistance and the production of inflammatory cytokines. It is therefore of primary importance to deal with obesity by effective means which, combined with diet and lifestyle changes, support the body during the weight loss and maintenance stages.

Specific inhibitors of some enzymatic systems involved in the etiopathogenesis of obesity have been identified, in particular pancreatic lipase inhibitors of microbial origin (Orlistat) and serotonin reuptake inhibitors such as rimonabant and sibutramine. However, the side effects of said medicaments are such that they can only be used in serious cases and only by a small part of the population, their use for the youngest patients being particularly unsuitable.

WO2008107184 discloses compositions containing *Cynara scolymus* and *Phaseolus vulgaris* extracts for the treatment of obesity.

However, there is still a need for more effective alternative remedies which are easier to manage in the treatment of obesity.

DESCRIPTION OF THE INVENTION

It has now been found that a combination of medicinal plant extracts causes a reduction in body weight by burning the fats accumulated in reserve organs. The combination according to the invention comprises extracts of *Phaseolus vulgaris, Cynara scolymus, Vitis vinifera, Echinacea angustifolia* and optionally, *Panax ginseng*.

The invention therefore relates to pharmaceutical or nutraceutical compositions comprising said extracts, for use in the prevention and treatment of obesity and excess weight in general, and in young people in particular.

The compositions according to the invention contain α-glucosidase and/or α-amylase inhibitors, gastric and pancreatic lipase inhibitors, anti-free radical compounds, anti-inflammatories and compounds able to increase energy expenditure. The compositions according to the invention therefore reduce the absorption and transport of the glucose and lipids present in the diet, and stimulate the energy metabolism.

In particular, *Phaseolus vulgaris* extract possesses inhibiting activity against α-amylase, an enzyme that demolishes starches, thus promoting glucose absorption. The extract modulates the appetite, as it increases the feeling of fullness due to the presence of phytohaemagglutinin which binds the brush border membranes of the intestinal cells, thus stimulating the release of cholecystokinin (CCK) and glucagon-like peptides [Carai M. A M. Brit. J. of Nutr. 3; 1-7, 2011].

*Cynara scolymus* extract has a high content of caffeoylquinic acids, which are known to inhibit the transport of glucose, and consequently its absorption in the gastrointestinal tract. Low glucose absorption is a crucial parameter to prevent the postprandial blood glucose peak.

*Vitis vinifera* seed extract has inhibiting properties against α-glucosidase and pancreatic lipase. The modulation of said enzymes is an extremely important aspect in controlling obesity. In particular, inhibition of pancreatic lipases, enzymes that hydrolyse the lipids in the intestinal tract and promote their absorption, is essential for the control of obesity. Grape seeds extract inhibits lipoprotein lipase (LPL), which releases lipids into the plasma, thus helping to reduce lipid absorption and improve the blood lipid profile. This activity is synergic with the anti-free radical activity typically present after a meal rich in fats, promoting the maintenance of a good state of the blood vessel endothelium and a consequent reduction of the risk of cardiovascular and metabolic diseases [Moreno D. A., Nutrition, 19; 876-879, 2003].

The lipophilic extract of *Echinacea* spp., preferably *Echinacea angustifolia*, contains alkylamides with activity that inhibits the release of pro-inflammatory cytokines (IL-6 and IL-8). Excess weight/obesity is often accompanied by a generalised inflammatory state wherein inflammatory cytokines contribute to significantly inducing the state known as metabolic syndrome.

*Echinacea* alkylamides, due to their lipophilic nature and rapid absorption, synergically enhance the anti-inflammatory activity of other compounds contained in *Cynara scolymus* and *Vitis vinifera* extracts.

*Panax ginseng* (or *Panax quinquefolium* or other species containing the same active substances) is a known "adaptogen", namely a plant that favourably modifies many stress conditions in the body. Ginsenosides, considered to be the main active substances in the extract, inhibit pancreatic lipase by reducing the absorption of fats and improving the blood lipid profile. Ginsenosides are also inducers of particular proteins (UCP-2) which increase energy consumption with thermogenic activity, inducers of the carnitine-palmitoyl-transferase enzyme, which has an antiadipogenic effect, and stimulate the synthesis of neuropeptide Y antagonists with an anorexigenic effect.

Ginseng also stimulates protein synthesis in the liver, which can improve the lipoprotein ratio in accumulation areas [Seung-Hwang K., Pharm. Res., 48; 511-513, 2003].

Said extracts are known and available on the market. A *Cynara scolymus* extract is disclosed, for example, in WO 2007/006391, the preparation of a *Phaseolus vulgaris* extract is disclosed in WO2007071334, the preparation of *Echinacea* extracts is described in EP1539203, and the preparation of *Vitis vinifera* extracts is disclosed in U.S. Pat. No. 5,484,594.

Particularly preferred are *Phaseolus vulgaris* extract with an α-amylase inhibitor content of 300 μg/mg and a lectin value of 10000 U/mg, a *Cynara scolymus* extract with a caffeoylquinic acid content ranging between 20 and 70%, preferably 35%, and a *Panax ginseng* extract having a ginsenoside content (determined by HPLC) of 7%.

The unit doses of the various extracts can vary within wide limits, in view of their high tolerability. In any event, the list below indicates the typical dose ranges that could be adapted according to the active ingredient content of the extracts, the particular form of administration and the therapeutic objective to be achieved (priming dose and maintenance dose, for example):

*Phaseolus vulgaris:* 50 to 200 mg, preferably 100 mg
*Cynara scolymus:* 50 to 200 mg;
*Echinacea angustifolia:* 10 to 50 mg;
*Vitis vinifera:* 100 to 250 mg;
*Panax ginseng:* 20 to 50 mg.

A particularly preferred composition contains:
100 mg of *Phaseolus vulgaris* extract with an α-amylase inhibitor content of 300 µg/mg and a lectin value of 10000 U/mg.
40 mg of *Panax ginseng* extract with a ginsenoside content (determined by HPLC) of 7%, and 50 to 200 mg, preferably 100 mg, of a *Cynara scolymus* extract with a caffeoylquinic acid content of 20 to 70%, preferably 35%;
25 mg of *Echinacea angustifolia* extract;
200 mg of *Vitis vinifera* pips.

The formulations will also contain conventional excipients, and optionally lipophilic extracts of *Foeniculum vulgare* or *Melissa officinalis*, which latter reduce the flatulence and spasms induced by excess gas production.

The formulations will typically be administered once or a twice a day, preferably twice a day. If *Panax ginseng* is present, the product will preferably be administered during the daytime to avoid adverse effects on sleep.

The compositions according to the invention, as well as reducing the postprandial blood glucose level, also cause a surprising reduction in the daily systemic blood glucose level. The resulting blood insulin level favourably influences the glycolipid metabolism, which is a pre-requisite for controlling excess weight. The compositions according to the invention also cause an unexpected increase in HDL cholesterol in hyperlipaemic subjects and in those whose HDL cholesterol level is below normal following treatment with cholesterol-lowering medicaments. In particular, a reduction of about 20% in total cholesterol and LDL cholesterol, and a significant increase of over 20% in HDL cholesterol, was observed. In a case study of patients with total cholesterol levels ranging from 220 to 280 mg/dl, said increase was constant over time, and appeared to be much more marked than reported for traditional herbal preparations to date.

The compositions according to the invention act on the whole metabolic profile of both children and adults, and are particularly suitable for the treatment of obesity, excess weight, metabolic syndrome and type 2 diabetes, especially in women.

The different activities of the constituents of the compositions according to the invention, which modify the absorption of fats and carbohydrates, the blood glucose and blood lipid levels, accumulation of fats in the tissues, the feeling of fullness and psychological stimulus, combine to provide an effective solution to the therapeutic problem of obesity, especially in young people.

Moreover, the protective activity of the extracts attenuates the oxidative and inflammatory processes which, in time, can cause permanent damage to the circulatory apparatus. Finally, the formulations according to the invention have the advantage of acting synergically on a number of factors without aggressive action on a single biological target, thus avoiding the major physical and neurological side effects that cause most failures of conventional treatments.

According to a preferred aspect, the compositions according to the invention will be formulated as capsules, single-dose sachets, conventional or gastroprotected tablets, to promote topical local activity while leaving the digestive function unchanged at stomach level.

According to a further aspect, the compositions according to the invention may be administered together with other substances having a useful or complementary activity. In paediatric medicine, preference will be given to sachet formulations due to their ease of administration, while capsules or tablets will be used for adults and school-age children.

The compositions according to the invention will be formulated according to conventional methods, such as those described in "Remington's Pharmaceutical Handbook", Mack Publishing Co., N.Y., USA. In particular, the compositions according to the invention will be formulated by conventional plant ingredient formulation techniques, which require particular care to be taken to avoid interactions with the excipients and the capsule matrices. Examples of oral formulations are tablets, dragées, soft and hard gelatin capsules, and cellulose capsules.

The examples set out below further illustrate the invention.

EXAMPLE 1

Tablets

Extracts of:

| | |
|---|---|
| *Cynara scolymus* (caffeoylquinic acid 30%) | 200 mg |
| *Phaseolus vulgaris* | 100 mg |
| *Panax ginseng* | 100 mg |
| *Echinacea angustifolia* | 25 mg |
| *Vitis vinifera* | 200 mg |
| Microcrystalline cellulose | 310 mg |
| Sodium croscarmellose | 30 mg |
| Magnesium stearate | 8 mg |
| Silica | 8 mg |

EXAMPLE 2

Tablets

Extracts of:

| | |
|---|---|
| *Cynara scolymus* (caffeoylquinic acid 30%) | 200 mg |
| *Phaseolus vulgaris* | 100 mg |
| *Echinacea angustifolia* | 25 mg |
| *Vitis vinifera* | 200 mg |
| Microcrystalline cellulose | 410 mg |
| Sodium croscarmellose | 30 mg |
| Magnesium stearate | 8 mg |
| Silica | 8 mg |

EXAMPLE 3

A non-randomised open-label clinical trial was conducted to evaluate the activity of example 1 combined with example 2. The two tablets were administered at the main meals (1 with the midday meal and 2 with the evening meal) to a group of 10 young people (between 12 and 16 years old) using a Body Mass Index (BMI) of between 26 and 30 and absence of concomitant disorders as selection criteria.

5 groups were set up (group 1: 200 mg *Cynara sc.* and 100 mg *Phaseolus vulg.*, group 2: 100 mg *Panax Gin.*, group 3: 25 mg *Echinacea ang.*, group 4: 200 mg *Vitis vinif.*, group 5: ex. 1 and ex. 2 as described above) and the individual extracts were compared with the examples specified above, evaluating the blood cholesterol, blood triglycerides, blood glucose and BMI values before treatment and after 1 month's treatment.

TABLE 1

| Group | Mean value of total cholesterol before treatment | % variation in mean value of total cholesterol after 1 month's treatment | Mean value of LDL cholesterol before treatment | % variation in mean value of LDL cholesterol after 1 month's treatment | Mean value of HDL cholesterol before treatment | % variation in mean value of HDL cholesterol after 1 month's treatment |
|---|---|---|---|---|---|---|
| Group 1 (10 patients) | 267 | −4.5 | 172 | −3.2 | 35 | 3.8 |
| Group 2 (20 patients) | 278 | −4.1 | 188 | −5.2 | 34 | 6.5 |
| Group 3 (19 patients | 271 | −6.2 | 181 | −5.6 | 36 | 3.2 |
| Group 4 (23 patients | 265 | −0.5 | 175 | −0.1 | 37 | 0.6 |
| Group 5 (23 patients) | 275 | −23 | 198 | −20.88 | 33 | 22 |

TABLE 2

| Group | Mean value of triglycerides before treatment | % variation in mean value of triglycerides after 1 month's treatment | Mean value of blood glucose before treatment | % variation in mean value of blood glucose after 1 month's treatment | Mean BMI value | % variation in mean BMI value after one month's treatment |
|---|---|---|---|---|---|---|
| Group 1 (10 patients) | 285 | −4.2 | 142 | −11.2 | 28 | −2.1 |
| Group 2 (20 patients) | 256 | −8.0 | 131 | −4.9 | 29 | −1.2 |
| Group 2 (20 patients | 273 | −6.3 | 129 | −1.6 | 27 | −1.3 |
| Group 4 (23 patients | 277 | −1.2 | 134 | 1.3 | 27 | 0.5 |
| Group 5 (23 patients) | 267 | −41 | 130 | −22.4 | 28 | −8.5 |

The data reported above clearly indicate a significant reduction in the postprandial and fasting blood glucose levels and an improvement in the lipid and body weight profile (Body Mass Index) after one month's treatment. In all the treated subjects a reduction in appetite was observed, which is important in order to maintain the balance reached.

The invention claimed is:

1. A method of treatment of obesity and excess weight of a patient in need thereof, said method comprising:
 administering to said patient an effective amount of a composition comprising:
 a) from 50 mg to 200 mg extract of *Phaseolus vulgaris;*
 b) from 50 mg to 200 mg extract of *Cynara scolymus;*
 c) from 10 mg to 50 mg extract of *Echinacea angustifolia;*
 d) from 200 mg and 250 mg extract of *Vitis vinifera;* and optionally
 e) from 20 to 50 mg extract of *Panax ginseng;*
 mixed with suitable excipients; and
 treating said obesity and excess weight.

2. The method according to claim 1, wherein said composition is in the form of tablets, dragées, soft or hard gelatin capsules or cellulose capsules.

3. The method according to claim 1 wherein the extract of *Phaseolus vulgaris* has an α-amylase inhibitor content of 300 μg/mg and a lectin value of 10000 U/mg.

4. The method according to claim 1 wherein the extract of *Cynara scolymus* has a caffeoylquinic acid content ranging between 20 and 70%.

5. The method according to claim 1 wherein the extract of *Panax ginseng* has a ginsenoside content of 7% determined by HPLC.

6. The method according to claim 1, wherein said composition contains 100 mg of extract of *Phaseolus vulgaris,* 50 to 200 mg of an extract of *Cynara scolymus,* 25 mg of extract of *Echinacea angustifolia* and 200 mg of extract of *Vitis vinifera* seeds.

7. The method according to claim 6, wherein said composition also contains 40 mg of extract of *Panax ginseng.*

* * * * *